US010258552B2

(12) United States Patent
Li et al.

(10) Patent No.: US 10,258,552 B2
(45) Date of Patent: *Apr. 16, 2019

(54) COMPOSITION COMPRISING POLYMER PARTICLES, A HYDROCARBON-BASED OIL AND A SILICONE ELASTOMER, AND PROCESS USING THE SAME

(71) Applicant: L'OREAL, Paris (FR)

(72) Inventors: Hong Li, Paris (FR); Veronique Ferrari, Masisons-Alfort (FR)

(73) Assignee: L'OREAL, Paris (FR)

( * ) Notice: Subject to any disclaimer, the term of this patent is extended or adjusted under 35 U.S.C. 154(b) by 121 days.

This patent is subject to a terminal disclaimer.

(21) Appl. No.: 15/533,444

(22) PCT Filed: Dec. 11, 2015

(86) PCT No.: PCT/EP2015/079453
§ 371 (c)(1),
(2) Date: Jun. 6, 2017

(87) PCT Pub. No.: WO2016/096660
PCT Pub. Date: Jun. 23, 2016

(65) Prior Publication Data
US 2018/0028420 A1    Feb. 1, 2018

(30) Foreign Application Priority Data
Dec. 18, 2014 (FR) ................................ 14 62743

(51) Int. Cl.
| | | |
|---|---|---|
| *A61K 8/31* | (2006.01) | |
| *A61K 8/04* | (2006.01) | |
| *C08L 51/00* | (2006.01) | |
| *C08L 33/08* | (2006.01) | |
| *C08F 265/06* | (2006.01) | |
| *A61K 8/81* | (2006.01) | |
| *A61K 8/891* | (2006.01) | |
| *A61Q 1/02* | (2006.01) | |
| *A61Q 1/06* | (2006.01) | |
| *A61K 8/02* | (2006.01) | |

(52) U.S. Cl.
CPC .............. *A61K 8/31* (2013.01); *A61K 8/0241* (2013.01); *A61K 8/04* (2013.01); *A61K 8/8152* (2013.01); *A61K 8/8164* (2013.01); *A61K 8/891* (2013.01); *A61Q 1/02* (2013.01); *A61Q 1/06* (2013.01); *C08F 265/06* (2013.01); *C08L 33/08* (2013.01); *C08L 51/003* (2013.01); *A61K 2800/52* (2013.01); *A61K 2800/594* (2013.01); *A61K 2800/614* (2013.01); *A61K 2800/654* (2013.01)

(58) Field of Classification Search
CPC .......... A61K 8/31; A61K 8/04; A61K 8/8164; A61K 8/891; A61K 8/0241; A61K 8/8152; A61K 2800/594; A61K 2800/52; A61K 2800/654; A61K 2800/614; C08L 51/003; C08L 33/08; C08F 265/06; A61Q 1/02; A61Q 1/06

See application file for complete search history.

(56) References Cited

U.S. PATENT DOCUMENTS

| | | |
|---|---|---|
| 5,616,598 A | 4/1997 | Lion et al. |
| 5,851,517 A | 12/1998 | Mougin et al. |
| 5,945,095 A | 8/1999 | Mougin et al. |
| 2004/0137028 A1 | 7/2004 | de la Poterie |
| 2009/0196839 A1 | 8/2009 | Farcet |
| 2011/0243864 A1 | 10/2011 | Farcet et al. |

FOREIGN PATENT DOCUMENTS

| | | |
|---|---|---|
| EP | 0 749 746 | 12/1996 |
| EP | 0 749 747 | 12/1996 |
| FR | 2 785 530 | 5/2000 |
| FR | 2 880 267 A1 | 7/2006 |
| FR | 2 927 082 A1 | 8/2009 |
| FR | 2 937 645 | 4/2010 |
| FR | 2 972 630 A1 | 9/2012 |
| FR | 2 972 631 A1 | 9/2012 |
| JP | 2007/132971 A1 | 11/2007 |
| JP | 2013-209296 A | 10/2013 |

OTHER PUBLICATIONS

U.S. Appl. No. 14/575,259, filed Dec. 18, 2014, 2016/0175204, Rita Jaky El-Khouri.
U.S. Appl. No. 14/575,419, filed Dec. 18, 2014, 2016/0175230, Susan Halpern-Chirch.
U.S. Appl. No. 14/575,866, filed Dec. 18, 2014, US2016/0175232, Rita Jaky El-Khouri.
U.S. Appl. No. 14/974,531, filed Dec. 18, 2015, 2016/0184211, Roshanak Debeaud.
U.S. Appl. No. 14/974,706, filed Dec. 18, 2015, 2016/0175205, Roshanak Debeaud.
U.S. Appl. No. 15/105,293, filed Jun. 16, 2016, 2016/0317423, Julien Portal.

(Continued)

*Primary Examiner* — Trevor Love
(74) *Attorney, Agent, or Firm* — Oblon, McClelland, Maier & Neustadt, L.L.P.

(57) ABSTRACT

The present invention relates to a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one silicone elastomer conveyed in at least one second oil. The invention also relates to a process for making up and/or caring for keratin materials, in which said composition is applied.

16 Claims, No Drawings

(56) References Cited

OTHER PUBLICATIONS

U.S. Appl. No. 15/534,216, filed Jun. 8, 2017, Roshanak Debeaud.
U.S. Appl. No. 15/537,082, Laure Daubersies.
U.S. Appl. No. 15/537,422, Philippe Ilekti.
U.S. Appl. No. 15/537,423, Philippe Ilekti.
U.S. Appl. No. 15/535,963, filed Jun. 14, 2017, Laure Daubersies.
"KSG-320 Emulsifying Silicone Elastomer," Shin-Etsu Technical Data Sheet, Sep. 12, 2012, XP002746411, 2 pages.
International Search Report dated Feb. 3, 2016 in PCT/EP2015/079453 filed Dec. 11, 2015.

COMPOSITION COMPRISING POLYMER PARTICLES, A HYDROCARBON-BASED OIL AND A SILICONE ELASTOMER, AND PROCESS USING THE SAME

The present invention relates to compositions for making up and/or caring for human keratin materials, such as the skin, the lips and keratin fibres, in particular the eyelashes, comprising polymer particles, at least one hydrocarbon-based oil and at least one silicone elastomer conveyed in a second oil.

These compositions are well known and, although they have specific properties as a function of their use, there has been a very clear tendency for some time now to develop compositions whose persistence is improved. This avoids, on the one hand, the need to reapply the composition too often and, on the other hand, reduces transfer thereof onto supports with which the made-up areas might come into contact (clothing, cups, etc.) or else their removal via the action of sebum or external agents (food, rain, etc.).

This is why compositions for which this property is sought generally comprise at least one film-forming agent. This agent is quite often a polymer, which is in a solubilized form or dispersed in one of the phases of the composition. It allows the composition, once applied, to form after drying a film that is more cohesive, adherent and persistent on the support.

One of the problems encountered with such film-forming agents lies in the fact that they cause discomfort when used.

To begin with, it is not uncommon for their presence in compositions to make these compositions more tacky and often more difficult to apply.

In addition, this sensation of discomfort often persists after the composition has dried, since, once dry, the resulting deposit may leave a relatively rigid film, giving an impression of tautness and of drying-out, and occasionally causes a mask effect on the skin.

Compositions are thus sought which comprise at least one film-forming agent, which do not have the drawbacks mentioned above.

One subject of the invention is thus a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one silicone elastomer conveyed in at least one second oil.

A subject of the invention is also a process for making up and/or caring for keratin materials, in particular the skin, the lips and keratin fibres such as the eyelashes and the eyebrows, which consists in applying said composition.

The reason for this is that it has been found that the composition according to the invention leads to compositions that are easy to apply, with very good glidance, and which leave a sensation of softness on application. The deposits obtained are also non-tacky and remain comfortable while at the same time having good persistence.

However, other advantages will emerge more clearly on reading the description and the examples that follow.

It should be noted that, in the remainder of the description, unless otherwise indicated, the limits indicated for a range are included in that range.

The expressions "at least one" and "several" are used without distinction.

Hydrocarbon-Based Oil

The composition according to the invention comprises a hydrocarbon-based oil.

This oil may be volatile (saturating vapour pressure greater than or equal to 0.13 Pa measured at 25° C.) or non-volatile (saturating vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from hydrocarbon-based oils containing from 8 to 16 carbon atoms, and especially:

branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl, linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, the mixtures of n-undecane ($C_{11}$) and of n-tridecane ($C_{13}$) obtained in Examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol;

a mixture thereof.

More particularly, the content of hydrocarbon-based oil(s) ranges from 20% to 75% by weight, more particularly from 30% to 75% by weight and preferably from 40% to 60% by weight, relative to the weight of the composition.

This hydrocarbon-based oil may be provided totally or partly with the surface-stabilized polymer particles, in particular when these particles are introduced into the composition in the form of a pre-prepared dispersion of surface-stabilized polymer particles. In this case, the hydrocarbon-based oil present in the composition represents at least the non-aqueous medium of the dispersion of surface-stabilized polymer particles.

It may also be provided as a second oil conveying the silicone elastomer which will be described later.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 20% to 75% by weight, more particularly from 30% to 75% by weight and preferably from 40% to 60% by weight, relative to the weight of the composition.

It should be noted that the hydrocarbon-based oil(s), in particular isododecane, may constitute the only oil(s) of the composition, or may be present in a predominant weight content relative to the other oil(s) that may be present in the composition.

In accordance with a particular embodiment of the invention, if the composition contains one or more non-volatile oils, their content advantageously does not exceed 20% by weight and preferably does not exceed 15% by weight relative to the weight of the composition, and better still does not exceed 10% by weight relative to the weight of the composition.

In accordance with a more particular embodiment of the invention, the content of non-volatile hydrocarbon-based oil(s) does not exceed 5% and more particularly does not exceed 2% by weight relative to the weight of the composition, or even the composition is free of non-volatile oil(s).

Additional Silicone Oils

The composition according to the invention may also comprise at least one additional volatile or non-volatile, and preferably volatile, silicone oil.

The term "silicone oil" means an oil containing at least one silicon atom, and especially containing Si—O groups.

Among the additional volatile silicone oils that are suitable for use, examples that may be mentioned include volatile linear or cyclic silicone oils, especially those with a viscosity ≤8 centistokes ($8\times10^{-6}$ $m^2/s$) and especially containing from 2 to 7 silicon atoms, these silicones optionally comprising alkyl or alkoxy groups containing from 1 to 10 carbon atoms.

As volatile silicone oils that may be used, mention may be made especially of octamethylcyclotetrasiloxane, cyclopentadimethylsiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of non-phenyl non-volatile silicone oils, for instance polydimethylsiloxanes (PDMS), PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt.

Non-volatile phenyl silicone oils optionally comprising one or more dimethicone fragments ($—(CH_3)_2—SiO—$) are also suitable for use, for instance phenyl trimethicones, phenyl dimethicones, phenyltrimethylsiloxydiphenylsiloxanes, diphenyl dimethicones and trimethylpentaphenyltrisiloxane, and mixtures thereof.

If the composition comprises any, the content of additional, preferably volatile, silicone oil(s) is between 1% and 20% by weight and more particularly between 1% and 15% by weight relative to the weight of the composition.

Preferably, the composition does not comprise more than 10% by weight of additional non-volatile oil, relative to the weight of the composition, and preferably does not contain any.

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily medium, advantageously containing at least one hydrocarbon-based oil, as defined previously.

The polymer of the particles is a $C_1$-$C_4$ alkyl (meth) acrylate polymer. The $C_1$-$C_4$ alkyl (meth)acrylate monomers may be chosen from methyl (meth)acrylate, ethyl (meth) acrylate, n-propyl (meth)acrylate, isopropyl (meth)acrylate, n-butyl (meth)acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consists essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth) acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth) acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Advantageously, the tabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

The stabilizing polymer preferably has a number-average molecular weight ranging from 10 000 to 400 000 and preferably ranging from 20 000 to 200 000.

Preferably, the stabilizer is soluble in the hydrocarbon-based oil(s), in particular soluble in isododecane.

The stabilizer is in contact with the surface of the polymer particles and thus makes it possible to stabilize these particles at the surface, in particular in order to keep these particles in dispersion in the non-aqueous medium of the dispersion.

According to a theory which should not limit the scope of the present invention, the inventors put forward the hypothesis that the surface stabilization of the $C_1$-$C_4$ alkyl (meth) acrylate polymer particles results from a phenomenon of surface adsorption of the stabilizer onto the $C_1$-$C_4$ alkyl (meth)acrylate polymer particles.

Advantageously, the combination of the stabilizer+polymer of the particles present in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

Preferentially, the combination of the stabilizer+polymer of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer+polymer of the particles.

When the polymer particles are provided in the composition in the form of a pre-prepared dispersion, the oily medium of this polymer dispersion comprises a first hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a free-radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the free-radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles which is obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethyl hexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Moreover, the composition according to the invention advantageously comprises a content of surface-stabilized polymer particles, described previously, of between 5% and 55% by weight, advantageously 5% to 50% by weight, more particularly from 8% to 45% by weight and preferably from 10% to 40% by weight relative to the weight of the composition (content expressed as active material).

Plasticizer

According to one embodiment of the invention, the composition comprises at least one plasticizer. In the case where the polymer particles are provided in the form of a dispersion, the plasticizer is then advantageously present in said oily dispersion.

The plasticizer(s) may be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in a content ranging from 2% to 50% by weight relative to the total weight of the polymer particles, preferably from 2% to 40% by weight and even more particularly less than 20% by weight relative to the total weight of the polymer particles.

Silicone Elastomer Conveyed in an Oil

The composition according to the invention comprises at least one organopolysiloxane elastomer (also referred to as silicone elastomer) conveyed in a second oil, in particular in the form of an organopolysiloxane elastomer gel.

The term "organopolysiloxane elastomer" or "silicone elastomer" means a soft, deformable organopolysiloxane with viscoelastic properties and especially with the consistency of a sponge or soft sphere. Its modulus of elasticity is such that this material withstands deformation and has limited stretchability and contractability.

This material is capable of regaining its original shape after stretching.

It is more particularly a crosslinked silicone elastomer.

The silicone elastomer particles are conveyed in the form of a gel formed from an elastomeric organopolysiloxane included in at least one second oil chosen from hydrocarbon-based oils and silicone oils, or mixtures thereof.

In these gels, the organopolysiloxane particles are often non-spherical particles.

Preferably, said oil is a silicone oil and/or a hydrocarbon-based oil, which may be volatile or non-volatile. That which has been detailed previously regarding the additional hydrocarbon-based oils and silicone oils remains valid here and reference may be made thereto.

Preferably, the second oil, conveying the silicone elastomer, is chosen from volatile oils, more particularly from volatile hydrocarbon-based oils, preferably from volatile apolar hydrocarbon-based oils.

In accordance with a particularly advantageous embodiment of the invention, the second oil is the same as the hydrocarbon-based oil, and even more preferentially isododecane.

Non-Emulsifying Organopolysiloxane Elastomer

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysiloxane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst.

In particular, the organopolysiloxane elastomer may be obtained by reaction of dimethylpolysiloxane bearing dimethylvinylsiloxy end groups and of methylhydrogenopolysiloxane bearing trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, in particular a linear-chain or branched-chain structure or a cyclic structure.

Compound (A) may have a viscosity at 25° C. ranging from 1 to 50 000 centistokes, especially so as to be readily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group. Compound (A) may thus be chosen from trimethylsiloxy-terminated methylhydropolysiloxanes, trimethylsiloxy-terminated dimethylsiloxane/methyl-hydrosiloxane copolymers, and dimethylsiloxane/methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located at any position on the organopolysiloxane molecule but are preferably located at the ends of the organopolysiloxane molecule. The organopolysiloxane (B) may have a branched-chain, linear-chain, cyclic or network structure but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinylsiloxane copolymers comprising dimethylvinylsiloxy end groups, dimethylsiloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In particular, the organopolysiloxane elastomer may be obtained by reaction of dimethylpolysiloxane bearing dimethylvinylsiloxy end groups and of methylhydrogenopolysiloxane bearing trimethylsiloxy end groups, in the presence of a platinum catalyst.

According to another alternative form, compound (B) may be an unsaturated hydrocarbon-based compound containing at least two lower alkenyl groups (for example $C_2$-$C_4$); the lower alkenyl group may be chosen from vinyl, allyl and propenyl groups. These lower alkenyl groups may be located in any position of the molecule, but are preferably located at the ends. By way of example, mention may be made of hexadiene, in particular of 1,5-hexadiene. Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) to the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

The organopolysiloxane elastomer particles are preferably conveyed in the form of a gel formed from an elastomeric organopolysiloxane included in at least one hydrocarbon-based oil and/or one silicone oil, as defined below. In these gels, the organopolysiloxane particles may be spherical or non-spherical particles.

Spherical non-emulsifying elastomers that may be used include, for example, those sold under the names DC 9040, DC 9041, DC 9509, DC 9505 by the company Dow Corning.

Use may also be made of those sold under the names KSG-6, KSG-15, KSG-16, KSG-18, KSG-41, KSG-42, KSG-43 and KSG-44 by the company Shin-Etsu; Gransil SR 5CYC Gel, Gransil SR DMF 10 Gel and Gransil SR DC556 Gel from the company Gransil RPS from Grant Industries; 1229-02-167, 1229-02-168 and SFE 839 from the company General Electric.

According to a preferred embodiment, the composition according to the invention comprises, as organopolysiloxane elastomer conveyed in an oil, a non-emulsifying elastomer, preferably spherical, preferably chosen from the compounds sold under the names DC 9040, DC 9041, DC 9509, DC 9505 by the company Dow Corning.

According to one particular embodiment, elastomers may be used as a mixture with a cyclic silicone oil. An example that may be mentioned is the mixture of crosslinked organopolysiloxane/cyclopentasiloxane or a mixture of crosslinked organopolysiloxane/cyclohexasiloxane, for instance Gransil RPS D5 or Gransil RPS D6 from the company Grant Industries.

Emulsifying Organopolysiloxane Elastomer

According to another embodiment, the composition according to the invention comprises, as organopolysiloxane elastomer conveyed in a second oil, an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Preferably, the polyoxyalkylenated organopolysiloxane elastomer is obtained by crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for instance, in patents U.S. Pat. No. 5,236,986, U.S. Pat. No. 5,412,004 and US 2010/0 330 011.

In particular, the organopolysiloxane may be obtained by reaction of polyoxyalkylene (especially polyoxyethylene and/or polyoxypropylene) bearing dimethylvinylsiloxy end groups and of methylhydrogenopolysiloxane bearing trimethylsiloxy end groups, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes bearing trimethylsiloxy end groups, dimethylsiloxane-methylhydrogenosiloxane copolymers bearing trimethylsiloxy end groups, dimethylsiloxane-methylhydrogenosiloxane cyclic copolymers, and dimethylsiloxane-methylhydrogenosiloxane-laurylmethylsiloxane copolymers bearing trimethylsiloxy end groups.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in U.S. Pat. No. 5,236,986, U.S. Pat. No. 5,412,004, U.S. Pat. No. 5,837,793, U.S. Pat. No. 5,811,487 and US 2010/0 330 011, to which reference may be made.

Polyoxyalkylenated organopolysiloxane elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, and DC9010 and DC9011 by the company Dow Corning.

As suitable commercial polyether silicone elastomers, conveyed in an oil, mention may be made of the compound dimethicone/bis-isobutyl PPG-20 crosspolymer in isododecane, sold, for example, under the name Dow Corning EL-8050 ID Silicone Organic Elastomer Blend®, dimethicone/bis-isobutyl PPG-20 crosspolymer in isodecyl neopentanoate sold under the name Dow Corning EL-8051 IN Silicone Organic Elastomer Blend®, and dimethicone/bis-isobutyl PPG-20 crosspolymer in isohexadecane sold under the name Dow Corning EL-8052 IH Silicone Organic Elastomer Blend®.

Such compounds are especially described in document US 2010/0 330 011, to which reference may be made.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

Preferably, the organopolysiloxane elastomer is obtained by crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound with dimethylvinylsiloxy end groups and of methylhydrogenopolysiloxane with trimethylsiloxy end groups, in the presence of a platinum catalyst.

Compound (A2) is the base reagent for the formation of an organopolysiloxane elastomer, and the crosslinking is performed by addition reaction of compound (A2) with compound (B2) in the presence of the catalyst (C2).

Compound (A2) is in particular an organopolysiloxane containing at least two hydrogen atoms bonded to different silicon atoms in each molecule.

Compound (A2) may have any molecular structure, especially a linear-chain or branched-chain structure or a cyclic structure.

Compound (A2) may have a viscosity at 25° C. ranging from 1 to 50 000 centistokes, especially so as to be readily miscible with compound (B2).

The organic groups bonded to the silicon atoms in compound (A2) may be alkyl groups containing from 1 to 18 carbon atoms, such as methyl, ethyl, propyl, butyl, octyl, decyl, dodecyl (or lauryl), myristyl, cetyl or stearyl;

substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Preferably, said organic group is chosen from methyl, phenyl and lauryl groups.

Compound (A2) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers and dimethylsiloxane-methylhydrogenosiloxane-laurylmethylsiloxane copolymers containing trimethylsiloxy end groups.

Compound (B2) may be a polyglycerolated compound corresponding to formula (B') below:

$$C_mH_{2m-1}\text{—O—}[Gly]_n\text{-}C_mH_{2m-1} \tag{B'}$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5, and in particular n is equal to 3; Gly denotes:

—CH$_2$—CH(OH)—CH$_2$—O— or —CH$_2$—CH(CH$_2$OH)—O—

Advantageously, the sum of the number of ethylenic groups per molecule in compound (B2) and of the number of hydrogen atoms bonded to silicon atoms per molecule in compound (A2) is at least 4.

It is advantageous for compound (A2) to be added in an amount such that the molecular ratio between the total amount of hydrogen atoms bonded to silicon atoms in compound (A2) and the total amount of all the ethylenically unsaturated groups in compound (B2) is within the range from 1/1 to 20/1.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

The polyglycerolated organopolysiloxane elastomer is conveyed in gel form in at least one hydrocarbon-based oil and/or one silicone oil. In these gels, the polyglycerolated elastomer is often in the form of non-spherical particles.

Polyglycerolated organopolysiloxane elastomers that may be used include those sold under the names KSG-710, KSG-810, KSG-820, KSG-830 and KSG-840 by the company Shin-Etsu.

Preferably, the silicone elastomer conveyed in a second oil is an emulsifying elastomer, preferably comprising at least one hydrophilic chain and in particular polyoxyalkylene units.

In accordance with a particular embodiment of the invention, the second oil is chosen from volatile apolar hydrocarbon-based oils. Advantageously, the second oil is identical to the abovementioned hydrocarbon-based oil.

The content of silicone elastomer ranges between 1% and 12.5% by weight (expressed as active material), preferably from 2.5% to 10% by weight (expressed as active material), relative to the weight of the composition.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect waxes; rice wax, carnauba wax, candelilla wax, ouricury wax, esparto grass wax, cork fibre wax, sugar cane wax, Japan wax and sumac wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may in particular be mentioned are hydrogenated jojoba oil, isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, polypropylsilsesquioxane waxes (as described in patent WO 2005/100444), in particular with the $C_{30}$-$C_{45}$ alkyldimethylsilyl polypropylsilsesquioxane compound commercially available from Dow Corning under the brand name SW-8005 C30 Resin Wax.

The wax obtained by hydrogenation of olive oil esterified with the stearyl alcohol, sold under the name Phytowax Olive 18 L 57 or else the waxes obtained by hydrogenation of castor oil esterified with cetyl alcohol, sold under the names Phytowax Castor 16L64 and 22L73 by the company Sophim, may also be used. Such waxes are described in the application FR-A-2792190.

If the composition comprises any, their content advantageously represents less than 20% by weight, more particularly less than 10% by weight and preferably less than 5% by weight relative to the weight of the composition. Preferably, the composition is free of wax.

Dyestuffs

The compositions in accordance with the invention may comprise at least one dyestuff.

This (or these) dyestuff(s) are preferably chosen from pulverulent substances, liposoluble dyes and water-soluble dyes, and mixtures thereof. Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D & C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

These dyestuffs may be present in a content ranging from 0.1% to 40% by weight and more particularly from 0.5% to 22% by weight, relative to the total weight of the composition. According to a more particular variant of the invention, the content of dyestuffs represents from 0.8% to 15% by weight relative to the total weight of the composition.

Fibres

The composition according to the invention may also comprise at least one fibre.

The term "fibre" should be understood as meaning an object of length L and of diameter D such that L is greater than D and preferably very much greater than D, D being the diameter of the circle in which the cross section of the fibre is inscribed. In particular, the ratio L/D (or aspect ratio) is chosen in the range from 3.5 to 2500, preferably from 5 to 500 and better still from 5 to 150.

The fibres that may be used in the composition of the invention may be mineral or organic fibres, of synthetic or natural origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury.

In particular, the fibres have a length ranging from 1 μm to 10 mm, preferably from 0.1 mm to 5 mm and better still from 0.3 mm to 3 mm. They may have a cross section included within a circle with a diameter ranging from 2 nm to 500 μm, preferably ranging from 100 nm to 100 μm and better still from 1 μm to 50 μm. The weight or yarn count of fibres is often given in denier or decitex and represents the weight in grams per 9 km of yarn. Preferably, the fibres according to the invention have a yarn count chosen in the range from 0.01 to 10 denier, preferably from 0.1 to 2 denier and better still from 0.3 to 0.7 denier.

The fibres that may be used in the compositions according to the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in a content ranging from 0.5% to 30% by weight and more particularly from 2% to 25% by weight, relative to the weight of the composition. In accordance with a preferred embodiment of the invention, the content of fibres, if they are present, is less than or equal to 10% by weight and preferably less than or equal to 5% by weight, relative to the weight of the composition.

Additional Fillers

The term "fillers" should be understood as meaning colourless or white solid particles of any form, which are in a form that is insoluble and dispersed in the medium of the composition, and are of mineral or organic nature.

In the present patent application, "mineral filler" is understood to mean any mineral solid that is insoluble in the medium at room temperature (25° C.).

The term "mineral" refers to any compound or polymer whose chemical structure does not comprise any carbon atoms.

The fillers may or may not be surface-coated, and in particular they may be surface-treated with silicones, amino acids, fluoro derivatives or any other substance that promotes the dispersion and compatibility of the filler in the composition.

Such fillers are distinct from the mineral thickeners and also from the colouring agents described previously.

The fillers may be spherical, i.e. they may comprise at least a rounded general portion, preferably defining at least a sphere portion, preferably internally defining a concavity or a hollow (sphere, globules, bowls, horseshoe, and the like), or lamellar.

Such fillers are advantageously chosen from:
silica powders, such as the porous silica microspheres sold under the name Silica Beads SB-700 by the company Miyoshi or Sunsphere® H51 or Sunsphere® H33 by the company Asahi Glass; or the polydimethylsiloxane-coated amorphous silica microspheres sold under the name SA Sunsphere® H33 or SA Sunsphere® H53 by the company Asahi Glass, acrylic (co)polymer powders and derivatives thereof, in particular: the polymethyl methacrylate powder sold under the names Covabead® LH85 by the company Wackherr or Microsphere M-100® by the company Matsumoto, the polymethyl methacrylate/ethylene glycol dimethacrylate powder sold under the name Dow Corning 5640 Microsponge® Skin Oil Adsorber by the company Dow Corning or Ganzpearl® GMP-0820 by the company Ganz Chemical, the polyallyl methacrylate/ethylene glycol dimethacrylate powder sold under the name Poly-Pore® L200 or Poly-Pore® E200 by the company Amcol Health and Beauty Solutions Inc., the ethylene glycol dimethacrylate/lauryl methacrylate copolymer powder sold under the name Polytrap® 6603 by the company Dow Corning, the optionally crosslinked acrylate/alkyl acrylate copolymer crosslinked acrylate/ethylhexyl acrylate copolymer powder sold under the name Techpolymer ACP-8C by the company Sekisui Plastics, the ethylene/acrylate copolymer powder, such as the product sold under the name Flobeads® by the company Sumitomo Seika Chemicals, the expanded hollow particles of acrylonitrile (co)polymer sold under the name Expancel by Expancel or the microspheres sold under the name Micropearl F 80 ED® by the company Matsumoto, the polyurethane powders sold, for example, under the names Plastic Powder D-400, Plastic Powder CS-400, Plastic Powder D-800 and Plastic Powder T-75 by the company Toshiki, silicone powders advantageously chosen from: polymethylsilsesquioxane powders, in particular those sold under the name Tospearl, in particular Tospearl 145 A, by the company Momentive Performance Materials, organopolysiloxane elastomer powders coated with silicone resin, especially with silsesquioxane resin, such as the products sold under the name KSP-100, KSP-101, KSP-102, KSP-103, KSP-104 or KSP-105 by the company Shin-Etsu (INCI name: vinyl dimethicone/methicone silsesquioxane crosspolymer), silicone elastomer powders, such as the products sold under the name Trefil® Powder E-505C or Trefil® Powder E-506C by the company Dow Corning, powders of organosilicone particles, for example, in the form of bowls, such as those described in JP-2003 128 788 or JP-A-2000-191789 or also in patent application EP 1 579 841 and sold especially by the company Takemoto Oil & Fat, polyamide powders, such as Nylon® powders, in particular Nylon 12 powders, such as the nylon powders sold under the name Orgasol® 2002 EXS NAT COS by the company Arkema, powders of natural organic materials, such as polysaccharide powders and in particular starch powders, especially crosslinked or non-crosslinked corn, wheat or rice starch powders, powders of starch crosslinked by octenylsuccinic anhydride sold under the name Dry-Flo® by the company National Starch or powders of waxy corn starch, such as those which are sold under the names C* Gel 04201 by the company Cargill, Corn Starch B by the company Roquette and Organic Corn Starch by the company Draco Natural Products, spherical cellulose microparticles, such as Cellulobeads D-10, Cellulobeads D-5 and Cellulobeads USF, sold by the company Daito Kasei Kogyo, particles of N—(C$_8$-C$_{22}$ carbon atom acylated) amino acids; the amino acid may be, for example, lysine, glutamic acid or alanine, preferably lysine, for example Amihope LL by the company Ajinomoto or the product sold under the name Corum 5105 S by the company Corum, Perlite powders, such as those sold by the company World Minerals under the trade name Perlite P1430, Perlite P2550, Perlite P2040 or OpTiMat™ 1430 OR or 2550 OR. Europerl EMP-2 and Europerl 1 by the company lmerys, zeolites, such as the products sold by the company Zeochem under the names Zeoflair 300, Zeoflair 200, Zeoflair 100, X-Mol and X-Mol MT, calcium magnesium carbonate particles, such as those sold by the company Imerys under the name Calcidol, by the company LCW (Sensient) under the name Carbomat or by the company Omya under the name Omyacare S 60-AV.

Use may also be made of talc particles, for example sold under the names Luzenac Pharma M and UM by the company Imerys and Rose Talc and Talc SG-2000 by the company Nippon Talc; natural or synthetic mica particles, such as those sold under the names Mica M RP and Silk Mica by the company Merck, or the product sold under the name Sericite S-152-BC by the company Miyoshi Kasei; calcium carbonate and magnesium hydrogen carbonate; hydroxyapatite; boron nitride; fluorphlogopite; and mixtures thereof.

The spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine. The term "alkyl" mentioned in the compounds cited above especially denotes an alkyl group containing from 1 to 30 carbon atoms and preferably containing from 5 to 16 carbon atoms.

The composition advantageously has a content of additional filler(s) of between 0.5% and 30% by weight, more particularly from 2% to 15% by weight and preferably from 2% to 15% by weight, relative to the weight of the composition.

According to certain embodiments, the content of additional filler(s) is less than or equal to 10% by weight and preferably less than or equal to 5% by weight, relative to the weight of the composition. Preferably, the composition is free of fillers.

Optional Additives

The composition may comprise at least one optional ingredient chosen, for example, from film-forming agents other than the polymer particles described previously; antioxidants; preserving agents; fragrances; flavourings; neutralizers; emollients; organic thickeners; coalescers; moisturizers; vitamins, and mixtures thereof.

Needless to say, a person skilled in the art will take care to select the optional additional additives and/or the amount thereof such that the advantageous properties of the composition according to the invention are not, or are not substantially, adversely affected by the envisaged addition.

The compositions according to the invention are thus intended for caring for and/or making up keratin materials, in particular the skin or the lips, and also keratin fibres especially such as the eyelashes or the eyebrows. They advantageously contain a physiologically acceptable medium, in other words a medium that is compatible with the treated keratin materials.

The compositions according to the invention may be in fluid or solid form. Preferably, the compositions are in fluid form.

The term "fluid" refers to compositions for which it is possible to measure the viscosity at 25° C. and atmospheric pressure (1.013×10$^5$ Pa).

The compositions according to the invention may also be in anhydrous form, or in the form of oil-in-water or water-in-oil emulsions.

If the compositions comprise water, the water content advantageously does not exceed 15% by weight and even more particularly does not exceed 10% by weight relative to the weight of the composition. Preferably, if it is present, the water content does not exceed 5% by weight relative to the weight of the composition, and advantageously does not exceed 2% by weight, relative to the weight of the composition.

In accordance with a preferred embodiment of the invention, the compositions are anhydrous.

The term "anhydrous" means that water is not deliberately added to the compositions, but may be present in trace amount in the various compounds used in the compositions.

Advantageously, the composition according to the invention is a makeup composition, in particular a foundation, preferably in fluid form, or a lipstick in solid or fluid form.

Preferably, the hydrocarbon-based oil of the composition is chosen from volatile oils.

Furthermore, the composition according to the invention advantageously comprises dyestuffs. Reference may be made to the description as regards the nature and content of these compounds.

As regards foundations, the present invention more particularly concerns compositions whose viscosity ranges between 0.04 and 2 Pa·s (measured with a Rheomat RM 180 viscometer from Mettler (thermostatically set at 25° C. and 1.013×10$^5$ Pa)).

As regards the lip makeup compositions, they may be in a solid form (wand, dish) or in a fluid form (gloss) and preferably in fluid form. According to one variant of the invention, the composition comprises, besides the stabilized polymer particles and the block copolymer, at least one wax.

The invention is illustrated in more detail in the following examples.

All the percentages of reagents described in the examples are weight percentages.

SYNTHESIS EXAMPLES

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8 (Invention) and Examples 9 and 10 (Outside the Invention)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7 (Invention)

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8 (Invention)

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Example 9 (Outside the Invention)

Step 1: 48.5 g of isobornyl acrylate, 12 g of methyl acrylate, 0.6 g Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight.

A dispersion in isododecane of polymethyl acrylate particles stabilized with an isobornyl acrylate/methyl acrylate (80/20) statistical copolymer stabilizer was obtained.

Example 10 (Outside the Invention)

Step 1: 48.5 g of isobornyl acrylate, 21 g of methyl acrylate, 0.7 g Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight.

A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 7 to 10 was compared, and the following results were obtained.

| Example | Stabilizer | Stability |
| --- | --- | --- |
| 1 (invention) | 92 isobornyl acrylate/8 methyl acrylate | Stable |
| 7 (invention) | 100 isobornyl acrylate | Stable |
| 8 (invention) | 85 isobornyl acrylate/15 methyl acrylate | Stable |
| 9 (out of invention) | 80 isobornyl acrylate/20 methyl acrylate | Phase separation and setting to a solid |
| 10 (out of invention) | 70 isobornyl acrylate/30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio >80/20.

Examples 11 (Foundation)

The following compositions, the ingredients of which are given in the table below, are prepared.

The amounts are indicated as weight of starting materials.

| Ingredients | Amounts % in weight |
| --- | --- |
| (Methyl acrylate)-co-(isobornyl acrylate) copolymer in isododecane (according to Example 1) | 50 |
| Silicone elastomer: PEG-15/Lauryl dimethicone crosspolymer (at 25% by weight in isododecane; KSG 320 from Shin-Etsu) | 20 |
| Iron oxides (and) disodium stearoyl glutamate (and) aluminium hydroxide, (yellow) from Miyoshi Kasei | 1.58 |
| Iron oxides (and) disodium stearoyl glutamate (and) aluminium hydroxide, (red) from Miyoshi Kasei | 0.41 |
| Iron oxides (and) disodium stearoyl glutamate (and) aluminium hydroxide, (black) from Miyoshi Kasei | 0.15 |
| Titanium dioxide (and) disodium stearoyl glutamate (and) aluminium hydroxide, (white) from Miyoshi Kasei | 8.66 |
| Mica (Synafil S 1050 from Eckart) | 1.20 |
| Isododecane | qs |

Protocol for Preparing Said Compositions

The desired amount of polymer particle dispersion according to Synthesis Example 1 is weighed out, and the pigments are then added and the whole is homogenized (Rayneri blender, room temperature, 10 minutes).

The isododecane is then added, followed by the silicone elastomer (KSG-320) and the whole is homogenized for a further 10 minutes.

Evaluation of the Composition:

Tack Evaluation

The degree of tack on drying is evaluated in vivo:
- a dab (0.05 g) of formula is placed on the skin of the forearm,
- the formula is spread uniformly with the fingers, during the drying of the foundation, the person evaluating the composition touches the deposit of formula on the skin every 5 seconds to evaluate the degree of tack.

Results

A composition whose texture is fluid and which applies very easily with good glidance is obtained; the application time is short.

The deposit is very light and is not tacky during or after drying. It is homogeneous, matt and very soft.

No composition transfer marks are observed when the skin is rubbed with a paper handkerchief, when dry or in the presence of sebum.

Examples 12, 13 and 14: Lipsticks

The following compositions, the ingredients of which are collated in the table below, are prepared. The amounts are indicated as weight of starting materials, unless otherwise indicated.

| Ingredient | 12 | 13 | 14 |
|---|---|---|---|
| Silica silylate (Aerogel VM-2270; Dow Corning) | | | 1 |
| Red 7 | 1 | 1 | 1 |
| (Methyl acrylate)-co-(ethyl acrylate)-co-(isobornyl acrylate) copolymer in isododecane according to Example 2 | 58 | 58 | 58 |
| C30-45 Alkyldimethylsilyl polypropylsilsesquioxane (Dow Corning SW-8005 C30 Resin Wax from Dow Corning) | 0.59 | 0.59 | 0.59 |
| Silicone elastomer: PEG-15/lauryl dimethicone crosspolymer (at 25% by weight in isododecane; KSG 320 from Shin-Etsu) | 20 | 30 | 30 |
| Isododecane | 20.41 | 10.41 | 9.41 |

Protocol for Preparing Said Compositions

The pigment is ground in part of the isododecane three times with a three-roll mill so as to obtain a homogeneous, viscous paste.

The silicone wax is predissolved in part of the isododecane while hot so as to obtain a smooth, homogeneous mixture.

The stabilized polymer particle dispersion, the silica aerogel, the predissolved silicone wax, the silicone elastomer and the remaining amount of isododecane are placed in a heating pan.

The whole is heated until a homogeneous mixture is obtained, and the pigmentary paste is finally added with stirring.

If necessary, the isododecane is topped up to compensate for the evaporation.

Evaluation of the Compositions:

Oil Resistance Test:

The composition is applied to a Bioskin skin sample (25 μm thickness of the wet film).

The sample is left to dry for 24 hours at 35° C.

After the drying step, a drop of olive oil is placed on the film of composition and left for 10 minutes.

The oil is then wiped five times using cotton wool.

The integrity of the film after wiping with the cotton wool is evaluated to evaluate the oil resistance of the composition, on a scale ranging from 1 to 3 (1: excellent resistance, 2: intermediate resistance, and 3: poor resistance).

Transfer Test:

The composition is applied to a Bioskin skin sample (25 μm thickness of the wet film).

The sample is left to dry for 24 hours at 35° C.

After the drying step, a piece of adhesive tape is applied to the film of composition and removed at an angle of 180°.

The integrity of the film after removing the adhesive tape is evaluated on a scale ranging from 1 to 3 (1: intact film, 2: intermediate peeling, and 3: total peeling).

Results:

The compositions according to the invention are stable. They are easy to apply and leave a non-tacky, comfortable deposit (no impression of tautness or of drying-out), which shows very good oil resistance without any transfer.

The invention claimed is:

1. A composition, comprising:
   particles of at least one polymer that is surface-stabilized with a stabilizer;
   at least one hydrocarbon-based oil; and
   at least one silicone elastomer conveyed in at least one second oil,
   wherein
   the polymer of the particles is a $C_1$-$C_4$ alkyl (meth)acrylate polymer, and the stabilizer is an isobornyl (meth)acrylate polymer is selected from the group consisting of isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4.

2. The composition according to claim 1, wherein the polymer of the particles is a methyl acrylate and/or ethyl acrylate polymer.

3. The composition according to claim 1, wherein the polymer of the particles comprises an ethylenically unsaturated acid monomer or the anhydride thereof.

4. The composition according to claim 1, wherein the polymer of the particles comprises from 80% to 100% by weight of $C_1$-$C_4$ alkyl (meth)acrylate and from 0 to 20% by weight of ethylenically unsaturated acid monomer, relative to the total weight of the polymer.

5. The composition according to claim 1, wherein the polymer of the particles is selected from the group consisting of:
   methyl acrylate homopolymers;
   ethyl acrylate homopolymers;
   methyl acrylate/ethyl acrylate copolymers;
   methyl acrylate/ethyl acrylate/acrylic acid copolymers;
   methyl acrylate/ethyl acrylate/maleic anhydride copolymers;
   methyl acrylate/acrylic acid copolymers;
   ethyl acrylate/acrylic acid copolymers;
   methyl acrylate/maleic anhydride copolymers; and
   ethyl acrylate/maleic anhydride copolymers.

6. The composition according to claim 1, wherein the stabilizer is a statistical copolymer of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than or equal to 5.

7. The composition according to claim 1, wherein the stabilizer is selected from the group consisting of:
   isobornyl acrylate homopolymers;
   statistical copolymers of isobornyl acrylate/methyl acrylate;
   statistical copolymers of isobornyl acrylate/methyl acrylate/ethyl acrylate; and
   statistical copolymers of isobornyl methacrylate/methyl acrylate.

8. The composition according to claim 1, wherein the hydrocarbon-based oil is selected from the group consisting of apolar hydrocarbon-based oils.

9. The composition according to claim 1, wherein the content of hydrocarbon-based oil ranges from 30% to 75% by weight relative to the weight of the composition.

10. The composition according to claim 1, wherein the content of polymer particles surface-stabilized with a stabilizer, expressed as active material, represents from 5% to 55% by weight, expressed as polymer particle solids, relative to the weight of the composition.

11. The composition according to claim 1, wherein the second oil is a hydrocarbon based oil.

12. The composition according to claim 11, wherein the second oil is selected from the group consisting of volatile apolar hydrocarbon-based oils.

13. The composition according to claim 1, wherein the silicone elastomer is an emulsifying silicone elastomer.

14. The composition according to claim 1, comprising a content of silicone elastomer, expressed as active material, ranging from 1% to 12.5% by weight relative to the weight of the composition.

15. The composition according to claim 1, wherein the polymer particles surface-stabilized with a stabilizer are incorporated into the composition in the form of a dispersion in at least one hydrocarbon-based oil.

16. A process for making up and/or caring for the keratin materials, comprising applying the composition according to claim 1 to a keratin material.

* * * * *